(12) United States Patent
Hirose et al.

(10) Patent No.: US 9,095,256 B2
(45) Date of Patent: Aug. 4, 2015

(54) OPHTHALMOLOGIC IMAGING APPARATUS

(75) Inventors: Futoshi Hirose, Yokohama (JP);
Kazuhide Miyata, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/581,321

(22) PCT Filed: Mar. 8, 2011

(86) PCT No.: PCT/JP2011/001359
§ 371 (c)(1),
(2), (4) Date: Aug. 27, 2012

(87) PCT Pub. No.: WO2011/111376
PCT Pub. Date: Sep. 15, 2011

(65) Prior Publication Data
US 2012/0320338 A1 Dec. 20, 2012

(30) Foreign Application Priority Data

Mar. 12, 2010 (JP) .................................. 2010-056708

(51) Int. Cl.
*A61B 3/14* (2006.01)
*A61B 3/00* (2006.01)
*A61B 3/10* (2006.01)

(52) U.S. Cl.
CPC .............. *A61B 3/0091* (2013.01); *A61B 3/102* (2013.01)

(58) Field of Classification Search
CPC .... A61B 3/102; A61B 3/1225; A61B 5/0066; A61B 3/14; A61B 3/12; A61B 5/0073; A61B 3/024; A61B 3/1025; A61B 5/7257; A61B 3/0025; A61B 3/0058; A61B 3/0091; A61B 3/10; A61B 3/152; A61B 5/0033
USPC ......... 351/206, 205, 200, 208, 209, 221, 222, 351/245, 246, 203, 210, 216, 233
See application file for complete search history.

(56) References Cited

U.S. PATENT DOCUMENTS 8,096,658 B2   1/2012   Kikawa et al.
8,308,297 B2   11/2012  Hirose et al.
(Continued)

FOREIGN PATENT DOCUMENTS

EP   1 842 483 A1   10/2007
JP   10-295645 A    11/1998
(Continued)

OTHER PUBLICATIONS

Sep. 27, 2012 International Preliminary Report on Patentability in International Patent Appln. No. PCT/JP2011/001359.
(Continued)

*Primary Examiner* — Joseph P Martinez
*Assistant Examiner* — Brandi Thomas
(74) *Attorney, Agent, or Firm* — Fitzpatrick, Cella, Harper & Scinto

(57) ABSTRACT

Provided is an ophthalmologic imaging apparatus required by the position adjustment of a fixation lamp to be turned on, by a simple operation which includes: a scanning unit; an irradiation unit for irradiating an eye to be inspected with a measuring beam through the scanning unit; a fixation lamp; a lighting position changing unit for changing a lighting position of the fixation lamp; an optical path length difference changing unit for changing an optical path length difference between the measuring beam and a reference beam corresponding to the measuring beam based on the lighting position of the fixation lamp which is changed by the lighting position changing unit; and an acquisition unit for acquiring a tomographic image of the eye to be inspected based on a beam obtained by superimposing, on the reference beam, a return beam from the eye to be inspected, which is irradiated with the measuring beam.

23 Claims, 8 Drawing Sheets

(56) References Cited

U.S. PATENT DOCUMENTS

| | | |
|---|---|---|
| 8,534,835 B2 | 9/2013 | Murata et al. |
| 2007/0291277 A1* | 12/2007 | Everett et al. ................. 356/497 |
| 2009/0091766 A1 | 4/2009 | Hirose |
| 2009/0285354 A1 | 11/2009 | Hirose et al. |
| 2010/0149489 A1 | 6/2010 | Kikawa et al. |
| 2010/0321700 A1 | 12/2010 | Hirose et al. |
| 2011/0155916 A1 | 6/2011 | Furusawa et al. |
| 2011/0205490 A1 | 8/2011 | Murata et al. |
| 2011/0234975 A1 | 9/2011 | Hirose |
| 2011/0273668 A1 | 11/2011 | Hirose |
| 2011/0301455 A1 | 12/2011 | Numajiri et al. |
| 2012/0044455 A1 | 2/2012 | Hirose |
| 2012/0293770 A1 | 11/2012 | Hirose |

FOREIGN PATENT DOCUMENTS

| | | | |
|---|---|---|---|
| JP | 2009-160190 | * 12/2007 | ............... A61B 3/12 |
| JP | 2008-289579 A | 12/2008 | |
| JP | 2009-160190 A | 7/2009 | |
| JP | 2011-172822 A | 9/2011 | |

OTHER PUBLICATIONS

Jun. 8, 2011 International Search Report and Written Opinion in PCT/JP2011/001359.

* cited by examiner

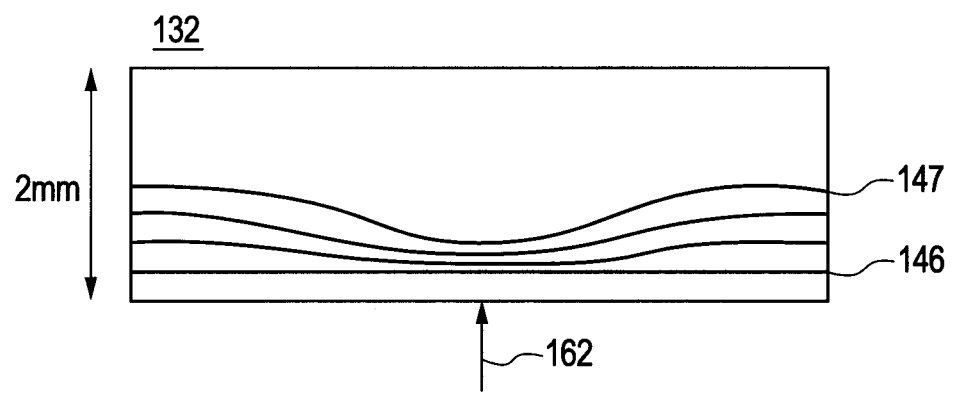
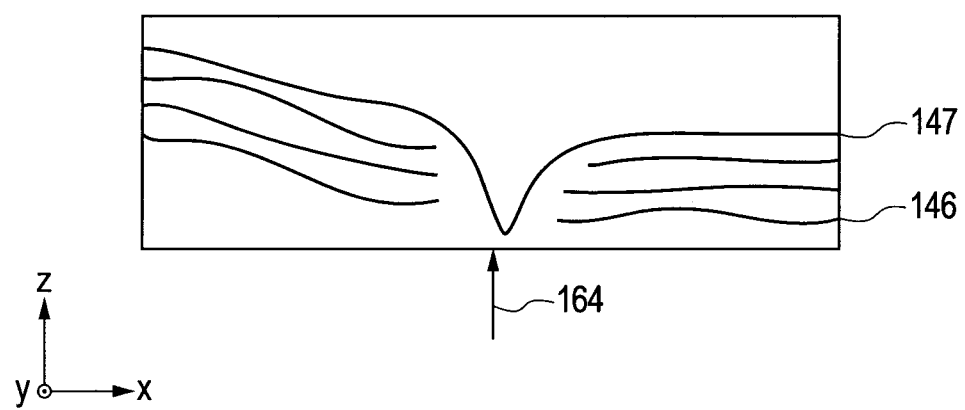

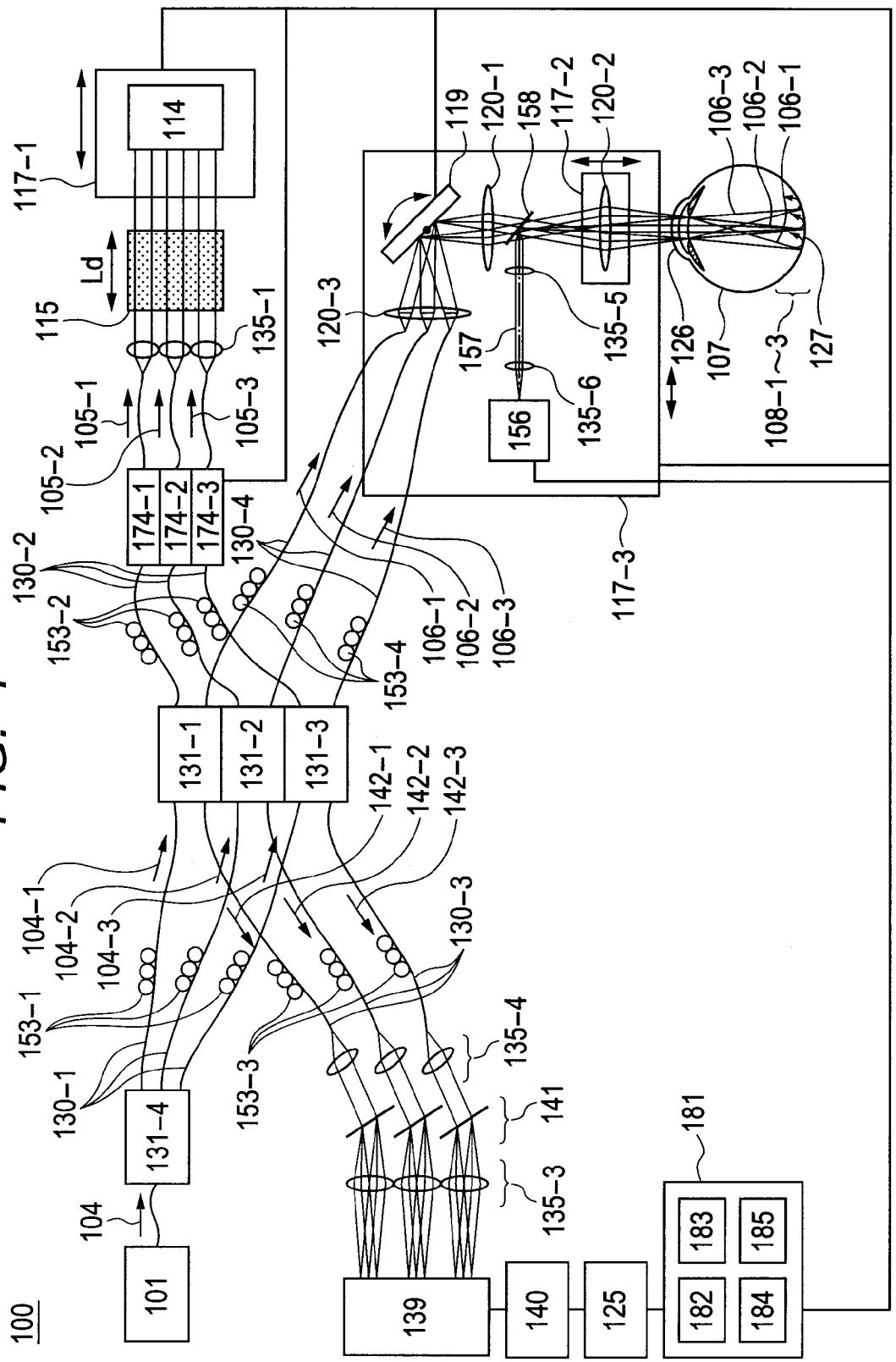

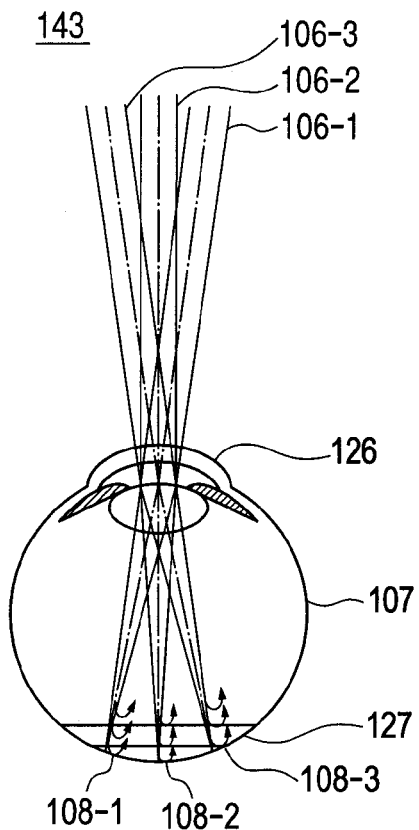
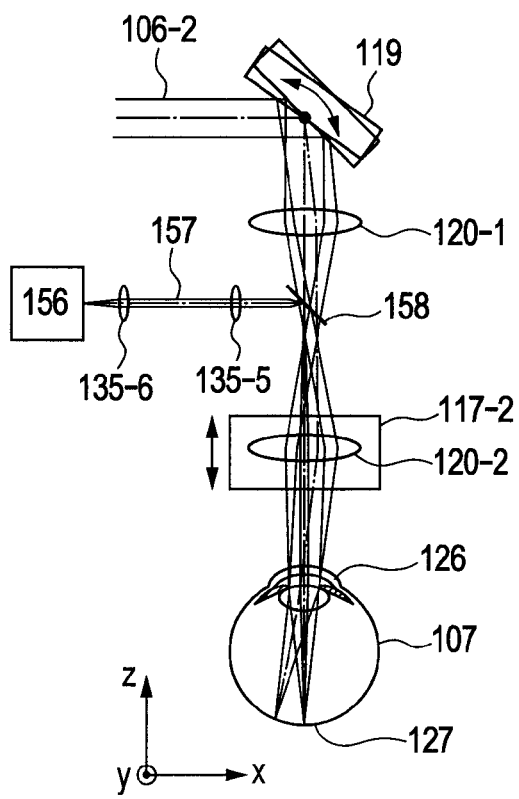
FIG. 8A
FIG. 8B
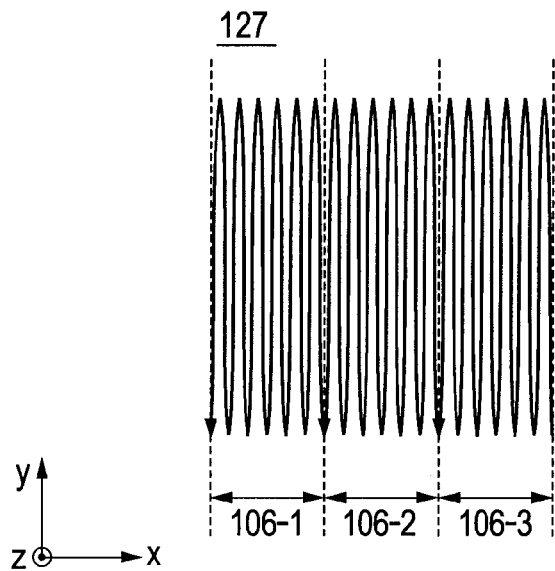
FIG. 8C

OPHTHALMOLOGIC IMAGING APPARATUS

TECHNICAL FIELD

The present invention relates to an ophthalmologic imaging apparatus for imaging an eye to be inspected.

BACKGROUND ART

There has been known an apparatus for acquiring a tomographic image of an eye to be inspected using optical coherence tomography (OCT) (also called OCT apparatus). A field angle is limited because of aberrations caused by optical members of the apparatus, and hence there is a limitation on a region on which imaging can be performed at a time. When a position of a fixation lamp to be turned on is adjusted, a line of sight of an eye to be inspected may be shifted. Therefore, when imaging is performed multiple times while the position of the fixation lamp to be turned on is adjusted, a fundus of the eye to be inspected may be imaged in a large region. During the imaging, when the line of sight is shifted while a cornea of the eye to be inspected is irradiated with a measuring beam, there is a possibility that the measuring beam is blocked by an iris of the eye to be inspected. In this case, the fundus is not irradiated with the measuring beam, and hence a suitable tomographic image cannot be acquired. Thus, PTL 1 discloses a fundus camera in which an optical axis of an optical system is shifted so as to align with an eye axis of the eye to be inspected based on the position of the fixation lamp to be turned on. This fundus camera ensures that the measuring beam is not blocked by the iris of the eye to be inspected, and hence a clear fundus image may be acquired.

PTL 2 discloses an OCT apparatus in which an arbitrary position of a tomographic image displayed on a display unit is specified and an optical path length of a reference beam is changed based on the specified position. This OCT apparatus ensures that an imaging position of the eye to be inspected in a depth direction (optical axis direction) thereof is adjusted.

CITATION LIST

Patent Literature

PTL 1: Japanese Patent Application Laid-Open No. H10-295645

PTL 2: Japanese Patent Application Laid-Open No. 2009-160190

A case where the position of the fixation lamp to be turned on is adjusted (or relative position between the optical axis of the optical system and the eye axis of the eye to be inspected is adjusted) in the OCT apparatus is considered. In this case, a distance between the cornea (anterior ocular segment) of the eye to be inspected and the fundus thereof is changed, and hence a coherence gate position (optical length difference between the reference beam and the measuring beam) is changed. This means that the position of the tomographic image displayed on the display unit is shifted to an upper side or lower side on a display area of the display unit, and hence there is a possibility that the tomographic image is located outside the display area. When the coherence gate position is distant from a region to be imaged, the resolution of the tomographic image degrades (or mirror image occurs). Therefore, it is necessary to maintain the coherence gate position relative to the region to be imaged as constant as possible. In the OCT apparatus, when an inspector separately performs the adjustment of the position of the fixation lamp to be turned on and the alignment of the eye to be inspected in the depth direction, the alignment operation is complicated.

SUMMARY OF INVENTION

Solution to Problem

In order to solve the above-mentioned problems, an ophthalmologic imaging apparatus according to the present invention includes: a scanning unit; an irradiation unit for irradiating an eye to be inspected with a measuring beam through the scanning unit; a fixation lamp; a lighting position changing unit for changing a lighting position of the fixation lamp; an optical path length difference changing unit for changing an optical path length difference between the measuring beam and a reference beam corresponding to the measuring beam based on the lighting position of the fixation lamp which is changed by the lighting position changing unit; and an acquisition unit for acquiring a tomographic image of the eye to be inspected based on a beam obtained by superimposing, on the reference beam, a return beam from the eye to be inspected, which is irradiated with the measuring beam.

Advantageous Effects of Invention

According to the ophthalmologic imaging apparatus (OCT apparatus) of the present invention, the alignment of the eye to be inspected in the depth direction, which is required by the adjustment of the position of the fixation lamp to be turned on, may be performed by a simple operation.

Further features of the present invention will become apparent from the following description of exemplary embodiments with reference to the attached drawings.

BRIEF DESCRIPTION OF DRAWINGS

FIG. 5A illustrates the image acquisition procedure using the OCT apparatus according to the first embodiment of the present invention.

FIG. 5B illustrates the image acquisition procedure using the OCT apparatus according to the first embodiment of the present invention.

FIG. 7 illustrates an entire structure of an OCT apparatus according to a second embodiment of the present invention.

FIG. 8A illustrates an image acquisition method using the OCT apparatus according to the second embodiment of the present invention.

FIG. 8B illustrates an image acquisition method using the OCT apparatus according to the second embodiment of the present invention.

FIG. 8C illustrates an image acquisition method using the OCT apparatus according to the second embodiment of the present invention.

DESCRIPTION OF EMBODIMENTS

The present invention is described with reference to the following embodiments.

First Embodiment

A first embodiment describes an OCT apparatus to which a structure of an optical tomographic imaging apparatus according to the present invention is applied.

In this embodiment, the optical tomographic imaging apparatus is provided in which an object is irradiated with a measuring beam from a light source and a tomographic image of the object is acquired based on an intensity of a return beam which is the measuring beam reflected in the object.

The OCT apparatus includes a fixation lamp. An optical path length of a reference beam path is adjusted based on a lighting position of the fixation lamp.

First, a schematic entire structure of the OCT apparatus according to this embodiment is specifically described with reference to FIGS. 1A and 1B.

Figure 1A:
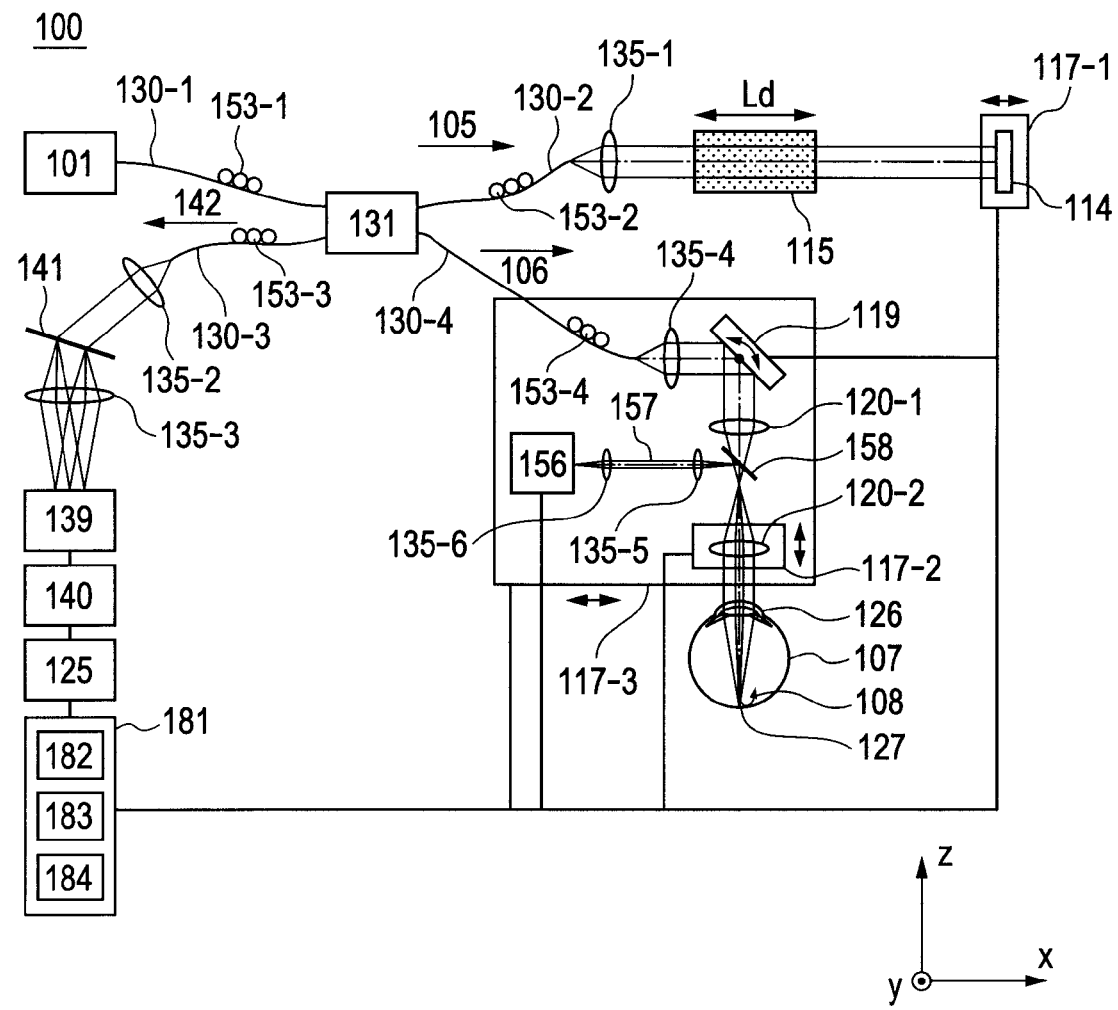
FIG. 1A illustrates an entire structure of an optical coherent tomography (OCT) apparatus according to a first embodiment of the present invention.

As illustrated in FIG. 1A, an OCT apparatus 100 according to this embodiment serves as a Michelson interferometer as a whole.

In FIG. 1A, a beam emitted from a light source 101 is divided into a reference beam 105 and a measuring beam 106 at a ratio of 90:10 through a single-mode fiber 130-1 and an optical coupler 131.

The measuring beam 106 is guided to an eye to be inspected 107 which is an observation object through a single-mode fiber 130-4, an XY-scanner 119, and lenses 120-1 and 120-2. A fixation lamp 156 is provided. Light flux 157 from the fixation lamp 156 acts to urge the fixation or rotation of the eye to be inspected 107. This is a feature of the first embodiment.

The measuring beam 106 is reflected or scattered in the eye to be inspected 107 which is the observation object, returned as a return beam 108, and combined by the optical coupler 131 on the reference beam 105 traveling through the reference beam path. Polarization controllers 153-1, 153-2, 153-3, and 153-4 adjust a polarization state of the measuring beam 106 and a polarization state of the reference beam 105.

After the reference beam 105 and the return beam 108 are combined on each other, a combined beam is spectrally separated for each wavelength by a transmission type grating 141 and enters a line camera 139.

The line camera 139 converts a light intensity into a voltage signal for each position (wavelength). The voltage signal is used to form a tomographic image of the eye to be inspected 107 by a personal computer 125.

An electric stage 117-1, the XY-scanner 119, and the fixation lamp 156 are drive-controlled by the personal computer 125 through a driver section 181.

Next, details of the light source 101 are described.

The light source 101 is a super luminescent diode (SLD) serving as a typical low-coherent light source.

A wavelength of the light source 101 is 830 nm and a bandwidth thereof is 50 nm.

The bandwidth is an important parameter because the resolution of an acquired tomographic image in an optical axis direction is affected by the bandwidth.

In this embodiment, the SLD is selected as a type of the light source 101. Any types of light source may be used as long as the light source can emit low-coherent light. An amplified spontaneous emission (ASE) light source may be used.

In view of the measurement of the eye, a suitable wavelength is a near infrared light wavelength. The wavelength affects the resolution of the acquired tomographic image in a lateral direction, and hence a minimum wavelength is desired. Therefore, in this embodiment, the wavelength is set to 830 nm.

Another wavelength may be selected depending on a measurement area of the observation object. The beam emitted from the light source 101 is guided to the optical coupler 131 through the single-mode fiber 130-1.

Next, an optical path of the reference beam 105 is described.

The reference beam 105 obtained by division by the optical coupler 131 is guided to a lens 135-1 through a single-mode fiber 130-2 and adjusted to become a parallel beam having a beam diameter of 4 mm. Then, the reference beam 105 is guided to a mirror 114 which is a reference mirror. An optical path length of the reference beam 105 is adjusted to be substantially equal to an optical path length of the measuring beam 106, and hence the reference beam 105 and the measuring beam 106 may be caused to interfere with each other. After that, the reference beam 105 is reflected on the mirror 114 and guided to the optical coupler 131 again. A dispersion compensation glass 115 through which the reference beam 105 passes is used to compensate with the reference beam 105 for dispersion that occurs when the measuring beam 106 travels to and from the eye to be inspected 107.

In this embodiment, assuming a typical value as an average diameter of eyes of the Japanese, a length Ld of the dispersion compensation glass 115 is set to 24 mm.

The electric stage (corresponding to reference beam path adjusting unit in this embodiment) 117-1 may be moved in a direction indicated by the arrows to be able to adjust the optical path length of the reference beam 105.

The electric stage 117-1 may be controlled by the personal computer 125 through an electric stage driver (corresponding to optical path length control unit in this embodiment) 183 included in the driver section 181.

Next, an optical path of the measuring beam 106 is described.

The measuring beam 106 obtained by division by the optical coupler 131 is guided to a lens 135-4 through the single-mode fiber 130-4 and adjusted to become a parallel beam having a beam diameter of 4 mm.

The measuring beam 106 is reflected on the XY-scanner 119, passes through a beam splitter 158 and the lenses 120-1 and 120-2, and enters the eye to be inspected 107.

For simplification, the XY-scanner 119 is illustrated as a single mirror. However, in an actual case, two mirrors, that is, an X-scanning mirror and a Y-scanning mirror, are disposed close to each other to raster-scan a retina 127 in a direction perpendicular to the optical axis. The center of the measuring beam 106 is adjusted to align with the center of rotation of the mirrors of the XY-scanner 119. The XY-scanner 119 is controlled by the personal computer 125 through an optical scanner driver 182 included in the driver section 181.

The lenses 120-1 and 120-2 correspond to an optical system for scanning the retina 127 and serve to scan the retina 127 with the measuring beam 106 about the vicinity of a cornea 126. A focal length of each of the lenses 120-1 and 120-2 is 50 mm.

An electric stage 117-2 may be moved in a direction indicated by the arrows to adjust and control the position of the associated lens 120-2. The electric stage 117-2 is controlled by the personal computer 125 through the electric stage driver 183 included in the driver section 181.

The position of the lens 120-2 may be adjusted, to thereby condense the measuring beam 106 to a predetermined layer of the retina 127 of the eye to be inspected 107 to observe the layer. Even when the eye to be inspected 107 has a refractive error, observation may be performed. When the measuring beam 106 enters the eye to be inspected 107, the measuring beam 106 is reflected or scattered on the retina 127 to become the return beam 108.

In this embodiment, the lens 120-2 is a spherical lens. A cylindrical lens may be used as the lens 120-2 depending on an optical aberration (refractive error) of the eye to be inspected 107. An additional lens may be provided on the optical path of the measuring beam 106.

The cylindrical lens is effective in a case where the eye to be inspected 107 is astigmatic.

The fixation lamp 156 includes a light-emitting type display module and has a display surface (15 mm×15 mm, 64×64 pixels) on a YZ-plane.

In this embodiment, any one of a liquid crystal array, an organic EL array, and an LED array is used. The eye to be inspected 107 gazes the light flux 157 from the fixation lamp 156 to urge the fixation or rotation of the eye to be inspected 107. For example, as illustrated in FIG. 1B, a cross pattern is blinked on the display surface of the fixation lamp 156 at an arbitrary lighting position 165.

The light flux 157 from the fixation lamp 156 is guided to the retina 127 through lenses 135-5 and 135-6, the beam splitter 158, and the lens 120-2. The lenses 135-5 and 135-6 are disposed so that the display surface of the fixation lamp 156 is optically conjugate with the retina 127. The fixation lamp 156 is controlled by the personal computer 125 through a fixation lamp driver 184 included in the driver section 181.

The lenses 120-1, 120-2, 135-4, 135-5, and 135-6, the optical scanner 119, the beam splitter 158, and the electric stage 117-2 are disposed on an electric stage 117-3.

The electric stage 117-3 is controlled by the personal computer 125 through the electric stage driver 183 included in the driver section 181. Therefore, the relative position between an optical axis of an irradiation unit for irradiating the eye to be inspected 107 with the measuring beam 106 through a scanning unit and an eye axis of the eye to be inspected 107 may be changed. In this embodiment, the optical axis of the irradiation unit is shifted relative to the eye axis of the eye to be inspected 107. Alternatively, the eye axis of the eye to be inspected 107 may be shifted relative to the optical axis of the irradiation unit.

The reference beam 105 and the return beam 108 are combined on each other by the optical coupler 131 and then divided at a ratio of 90:10.

A combined beam 142 is guided to a lens 135-2 through a single-mode fiber 130-3 and adjusted to become a parallel beam.

Then, the beam 142 is spectrally separated for each wavelength by the transmission type grating 141, condensed by a lens 135-3, and reaches the line camera 139.

Next, a structure of a measurement system of the OCT apparatus according to this embodiment is described.

The OCT apparatus 100 may acquire the tomographic image (OCT image) based on an intensity of an interference signal from a Michelson interference system.

The measurement system is described.

A light intensity of the combined beam 142 is converted into a voltage by the line camera 139 for each position (wavelength).

To be specific, an interference fringe of a spectral region on a wavelength axis is observed on the line camera 139.

An obtained voltage signal group is converted into digital values by a frame grabber 140, and data-processed by the personal computer 125 to form the tomographic image. The tomographic image is displayed on a display screen (also referred to as display unit) (not shown). It is preferred to provide a display control unit for causing the acquired tomographic image to be displayed on the display unit. The line camera 139 has 1,024 pixels and may obtain the intensity of the combined beam 142 for each wavelength (1,024 divisions).

Next, a method of acquiring a tomographic image (OCT image) using the OCT apparatus is described with reference to FIGS. 2A to 2C.

In the OCT apparatus 100, the XY scanner 119 is controlled and the interference fringe is obtained by the line camera 139, to thereby acquire the tomographic image of the retina 127. A method of acquiring the tomographic image (plane parallel to optical axis, namely, XZ-plane) of the retina 127 is described.

Figure 2A:
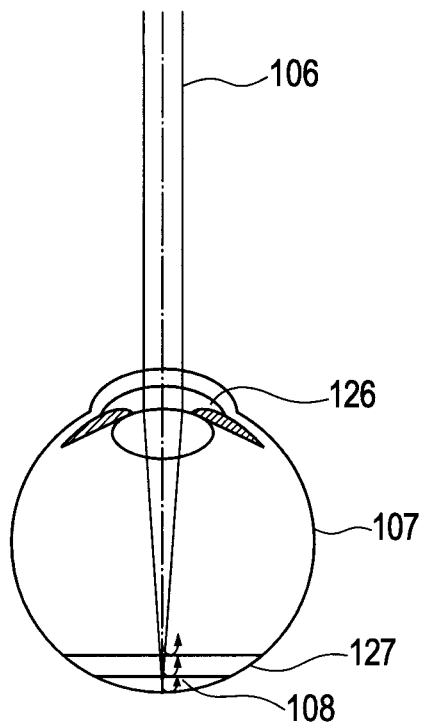
FIG. 2A illustrates an image acquisition method using the OCT apparatus according to the first embodiment of the present invention.

FIG. 2A is a schematic view illustrating the eye to be inspected 107, which is observed by the OCT apparatus 100.

As illustrated in FIG. 2A, when the measuring beam 106 passes through the cornea 126 and enters the retina 127, the measuring beam 106 is reflected or scattered in various positions to become the return beam 108. Then, the return beam 108 reaches the line camera 139 with time delays in the respective positions.

The bandwidth of the light source 101 is wide and the coherence length is short. Therefore, when the optical path length of the reference beam path is substantially equal to an optical path length of a measuring beam path, the interference fringe may be detected by the line camera 139.

As described above, the interference fringe of the spectral region on the wavelength axis is obtained by the line camera 139.

Then, the interference fringe which is information on the wavelength axis is converted into an interference fringe on an optical frequency axis in view of characteristics of the line camera 139 and the transmission type grating 141.

The interference fringe on the optical frequency axis, which is obtained by conversion, is subjected to inverse Fourier transformation to obtain information in a depth direction.

Figure 2B:
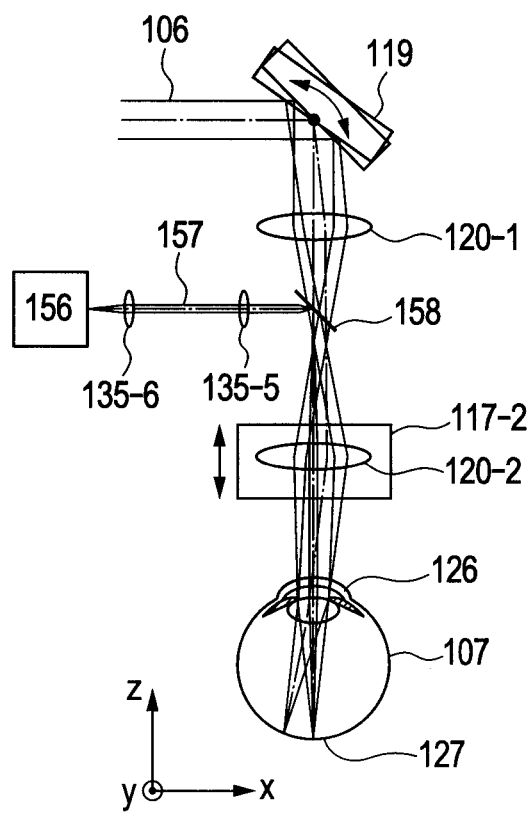
FIG. 2B illustrates an image acquisition method using the OCT apparatus according to the first embodiment of the present invention.

Further, as illustrated in FIG. 2B, when an interference fringe is detected while the XY-scanner 119 is driven, the interference fringe is obtained for each X-axis position. In other words, the information on the depth direction may be obtained for each X-axis position.

Figure 2C:
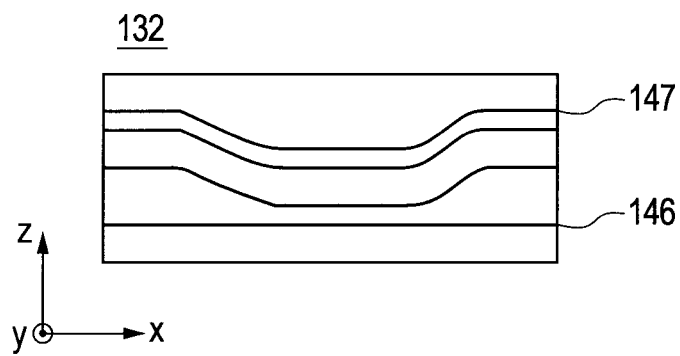
FIG. 2C illustrates an image acquisition method using the OCT apparatus according to the first embodiment of the present invention.

As a result, a two-dimensional intensity distribution of the return beam 108 on the XZ-plane is obtained, which is a tomographic image 132 (FIG. 2C).

As described above, the tomographic image 132 is originally an array of intensities of the return beam 108. For example, the intensities are displayed with gray scales.

The acquired tomographic image in which only the boundary thereof is emphasized is displayed. The tomographic image 132 includes a pigmented epithelial cells layer 146 and an inner boundary film 147.

Next, a tomographic image acquisition method using the OCT apparatus which is the feature of this embodiment is described with reference to mainly FIGS. 3A to 3D, 4A, 4B, 5A, 5B, and 6.

In a case where the fixation lamp 156 in the OCT apparatus is used to urge the rotation of the eye to be inspected 107, when the optical path length of the reference beam path is automatically adjusted, a tomographic image of the retina 127 may be efficiently acquired at a desired position. As a result, the tomographic image of the retina may be efficiently acquired at a wide field angle.

FIGS. 3A to 3D, 4A, 4B, 5A, and 5B illustrate a procedure for acquiring the tomographic image using the OCT apparatus 100. A case where a macula 162 and an optic disk 164 in the retina 127 are separately imaged is described. Another region of the retina 127 may also be imaged in the same manner.

In the tomographic image acquisition method, the following Steps (1) to (8) are performed, for example, continuously. Alternatively, processing may return to any step as appropriate. A computer may be used to automatically perform the following steps.

Figure 6:
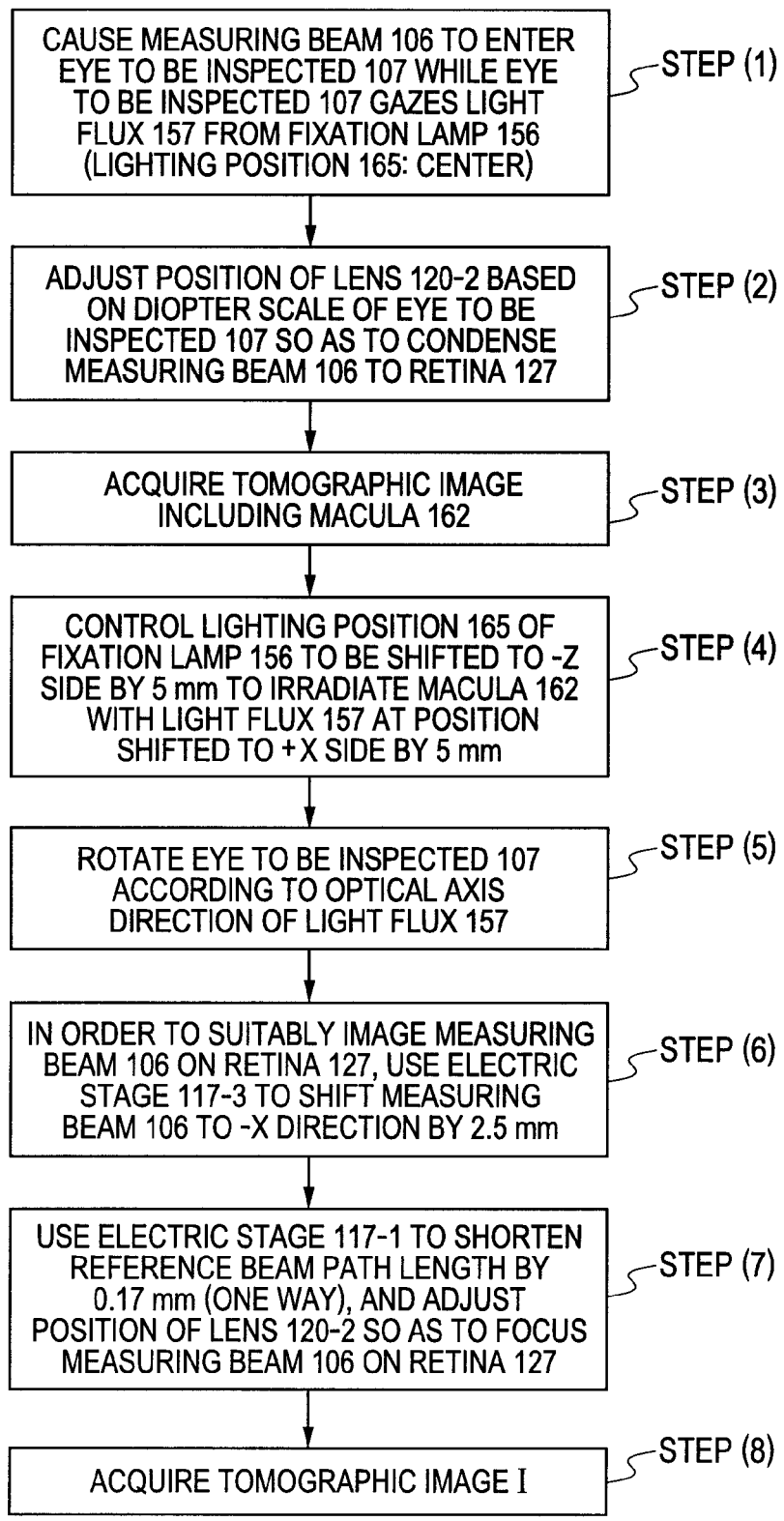
FIG. 6 illustrates the image acquisition procedure using the OCT apparatus according to the first embodiment of the present invention.

FIG. 6 is a flow chart illustrating the tomographic image acquisition method described above.

The following numerical values are examples obtained by calculation based on an average value of eye axis lengths of the Japanese by the inventors of the present invention, and desirably changed as appropriate based on the fixation state of the eye to be inspected and the position of the eye to be inspected.

When the eye to be inspected develops axial myopia, the numerical values are particularly desirably changed because of the remarkable influence thereof.

A diopter scale and the eye axis length of the eye to be inspected 107 are determined in advance. The diameter L of the eye to be inspected 107 is set to 24 mm based on the eye axis length measured in advance. A rotation point CR of the eye to be inspected 107 is assumed as the center of the eye to be inspected 107. A shape, the eye axis length, and the diopter scale of the eye to be inspected may be referred to as characteristics of the eye to be inspected. The eye to be inspected is generally an ellipse. Therefore, not only in the case where the position of the fixation lamp to be turned on is changed but also in the case where the relative position between the eye axis of the eye to be inspected and the optical axis of the irradiation unit is changed, the optical path length of the measuring beam is significantly changed. That is, the position of the tomographic image displayed on the display unit is significantly shifted to an upper side or a lower side on the display area of the display unit, and hence it is more likely to locate the tomographic image outside the display area. Therefore, when the relative position is adjusted, a coherence gate position (optical path length difference between measuring beam and reference beam) is desirably changed (based on characteristics of eye to be inspected). Thus, the tomographic image may be displayed on the display area of the display unit at an optimum position.

Figure 3A:
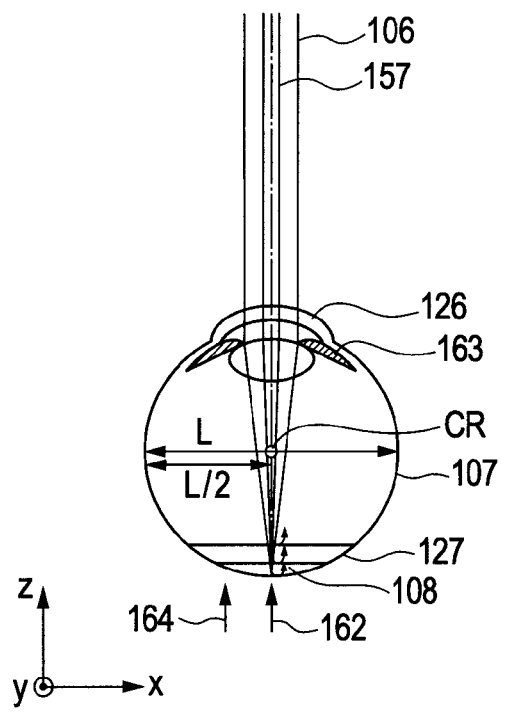
FIG. 3A illustrates an image acquisition procedure using the OCT apparatus according to the first embodiment of the present invention.

(1) While the eye to be inspected 107 gazes the light flux 157 from the fixation lamp 156, the measuring beam 106 is caused to enter the eye to be inspected 107 (FIG. 3A).

Figure 4A:
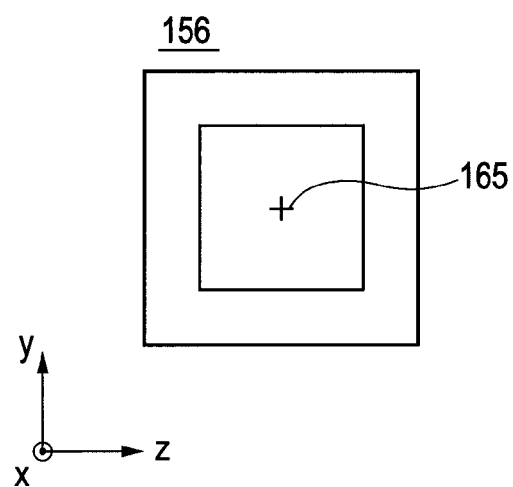
FIG. 4A illustrates the image acquisition procedure using the OCT apparatus according to the first embodiment of the present invention.

As illustrated in FIG. 4A, the lighting position 165 of the fixation lamp 156 is set to the center thereof as a lighting position for a first observation region.

(2) The position of the lens 120-2 is adjusted based on the diopter scale of the eye to be inspected 107 so as to condense the measuring beam 106 to the retina 127.

(3) In the state of Step (2), the tomographic image 132 including the macula 162 is acquired by the method described above (FIG. 5A).

An imaging range of the tomographic image 132 in a Z-direction is 2 mm.

Figure 3B:
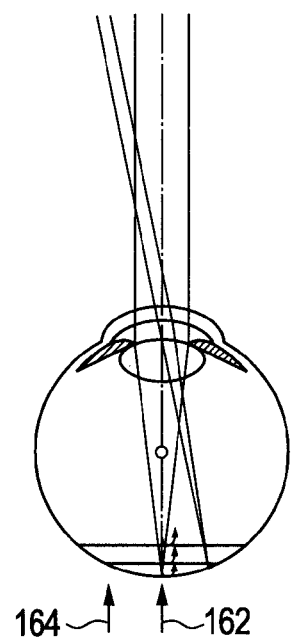
FIG. 3B illustrates an image acquisition procedure using the OCT apparatus according to the first embodiment of the present invention.

(4) Next, the lighting position 165 of the fixation lamp 156 is set to a position located at a predetermined distance as a lighting position for a second observation region. The lighting position 165 is controlled to be shifted to a –Z side by 5 mm to irradiate the macula 162 with the light flux 157 at a position shifted to a +X side by 5 mm (FIG. 3B).

Figure 4B:
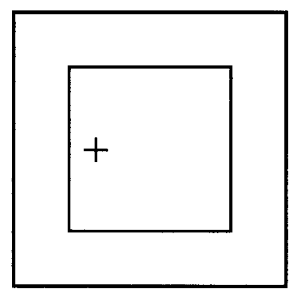
FIG. 4B illustrates the image acquisition procedure using the OCT apparatus according to the first embodiment of the present invention.

The shift distance of the lighting position 165 which is 5 mm is a general distance between the macula 162 and the optic disk 164 (FIG. 4B).

Figure 3C:
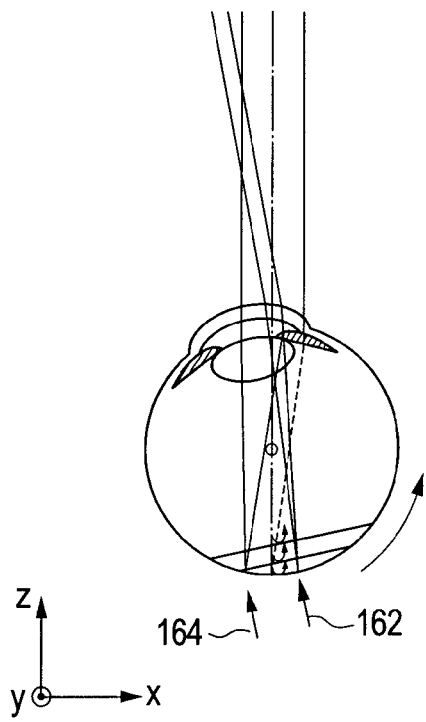
FIG. 3C illustrates an image acquisition procedure using the OCT apparatus according to the first embodiment of the present invention.

(5) The eye to be inspected 107 is rotated according to the optical axis direction of the light flux 157. In this case, the measuring beam 106 is eclipsed by an iris 163, and thus is not suitably imaged on the retina 127 (FIG. 3C).

Figure 3D:
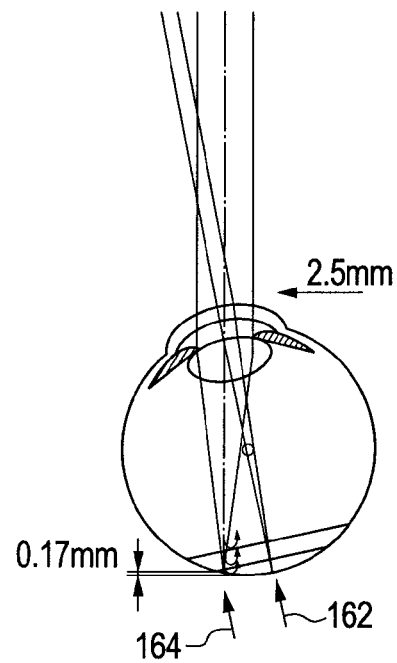
FIG. 3D illustrates an image acquisition procedure using the OCT apparatus according to the first embodiment of the present invention.

(6) In order to suitably image the measuring beam 106 on the retina 127, the electric stage 117-3 (FIG. 1A) is used to shift the measuring beam 106 to a –X direction by 2.5 mm, to thereby adjust the relative position between the measuring beam 106 and the eye to be inspected 107 (FIG. 3D). As compared with the case of FIG. 3A, the retina 127 is shifted in a +Z direction by approximately 0.17 mm.

(7) The electric stage 117-1 is used to shorten the reference beam path length by 0.17 mm (one way). The position of the lens 120-2 is adjusted so as to focus the measuring beam 106 on the retina 127.

(8) A tomographic image including the optic disk 164 is acquired by the method described above (FIG. 5B).

As described above, the coherence gate position (optical path length difference between measuring beam and reference beam) is adjusted based on the changed lighting position of the fixation lamp. Therefore, even when the imaging region is shifted in the optical axis direction by the rotation of the eye to be inspected, the imaging region is not located outside the imaging range and measurement sensitivity is not changed, and hence the tomographic image may be acquired with ease.

The electric stage 117-3 is used to change the relative position between the optical axis of the irradiation unit for irradiating the eye to be inspected with the measuring beam through the scanning unit and the eye axis of the eye to be inspected (relative position changing unit) based on the changed lighting position of the fixation lamp. Therefore, the measuring beam reaches the retina without being eclipsed by the iris, and hence the tomographic image may be acquired with ease.

When the lighting position of the fixation lamp is changed by a lighting position changing unit based on the characteristics (such as shape, eye axis length, and diopter scale) of the eye to be inspected, the optical path length difference may be suitably changed without depending on the eye to be inspected. Therefore, the tomographic image may be acquired at the suitable position of the eye to be inspected in the depth direction. When the optical path length difference is changed based on the characteristics of the eye to be inspected, the tomographic image may be acquired at the suitable position of the eye to be inspected in the depth direction without depending on the eye to be inspected.

When the fixation lamp lighting position changing step, the reference beam path length changing step, the measuring beam focusing step, and the tomographic image acquiring step are continuously performed, an optical tomographic imaging method of acquiring tomographic images of multiple imaging regions may be realized by a simple operation. In particular, when the measuring beam has a large beam diameter, the measuring beam focusing step is effective.

An optical tomographic imaging method as described below may be achieved as the optical tomographic imaging method.

When a tomographic image including the macula is to be acquired, the lighting position of the fixation lamp is set to a first lighting position. While the eye to be inspected gazes the fixation lamp, the measuring beam is caused to enter the eye to be inspected, to thereby acquire the tomographic image including the macula as a first tomographic image.

Next, when a tomographic image including the optic disk is to be acquired, the lighting position of the fixation lamp is changed to a second lighting position located at a predetermined distance from the first lighting position.

The relative position between the measuring beam and the eye to be inspected is adjusted based on the distance between the first lighting position and the second lighting position. The optical path length of the reference beam path is adjusted to an optical path length corresponding to the second observation region to acquire the tomographic image including the optic disk as a second tomographic image. A program for causing a computer (personal computer) to execute any of the optical tomographic imaging methods may be created and stored in a storage medium to be read by the computer.

Second Embodiment

In a second embodiment, an OCT apparatus to which the present invention is applied is described.

In this embodiment, a multi-beam OCT apparatus is particularly described in which three measuring beams may be used for high-speed imaging to simultaneously acquire three tomographic images. A case where the three measuring beams are used is described. The number of measuring beams may be further increased depending on a desired imaging speed.

The OCT apparatus includes a fixation lamp. Optical path lengths of multiple reference beams paths are adjusted based on a lighting position of the fixation lamp.

First, a schematic entire structure of the OCT apparatus according to this embodiment is specifically described with reference to FIG. 7.

Figure 1B:
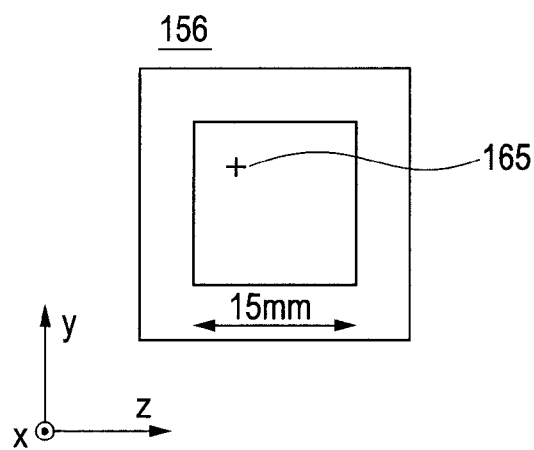
FIG. 1B illustrates an entire structure of an optical coherent tomography (OCT) apparatus according to a first embodiment of the present invention.

In FIG. 7, the same components as those of the first embodiment illustrated in FIGS. 1A and 1B are denoted by the same reference symbols, and hence duplicate description thereof is omitted.

As illustrated in FIG. 7, an OCT apparatus 100 according to this embodiment serves as a Michelson interferometer as a whole.

In FIG. 7, an emitted beam 104 which is a beam emitted from the light source 101 is divided into three emitted beams 104-1, 104-2, and 104-3 by an optical coupler 131-4. The respective emitted beams 104-1, 104-2, and 104-3 pass through polarization controllers 153-1 and are divided into reference beams 105-1, 105-2, and 105-3 and measuring beams 106-1, 106-2, and 106-3 at an intensity ratio of 90:10 by optical couplers 131-1, 131-2, and 131-3.

The measuring beams 106-1, 106-2, and 106-3 are reflected or scattered in the retina 127 of the eye to be inspected 107 which is the observation object, returned as return beams 108-1, 108-2, and 108-3, and combined on the reference beams 105-1, 105-2, and 105-3 by the optical couplers 131-1, 131-2, and 131-3.

After the reference beams 105-1, 105-2, and 105-3 and the return beams 108-1, 108-2, and 108-3 are combined on each other, combined beams are spectrally separated for each wavelength by the transmission type gratings 141 and enter the line camera 139. The line camera 139 converts light intensities into voltage signals for each position (wavelength). The voltage signals are used to form the tomographic images of the eye to be inspected 107.

The light source 101 is the same as in the first embodiment and thus the description thereof is omitted here.

Next, optical paths of the reference beams 105-1, 105-2, and 105-3 are described.

The reference beams 105-1, 105-2, and 105-3 obtained by division by the optical couplers 131-1, 131-2, and 131-3 pass through the polarization controllers 153-2 and fiber length variable devices 174-1, 174-2, and 174-3 and are converted into parallel beams having a diameter of 1 mm by lenses 135-1 to be emitted.

After that, the reference beams 105-1, 105-2, and 105-3 pass through the dispersion compensation glass 115 and is guided to the mirror 114. Then, the reference beams 105-1, 105-2, and 105-3 are turned by the mirror 114 and travel to the optical couplers 131-1, 131-2, and 131-3 again.

After that, the reference beams 105-1, 105-2, and 105-3 pass through the optical couplers 131-1, 131-2, and 131-3, and are guided to the line camera 139.

The fiber length variable devices 174-1, 174-2, and 174-3 are provided to finely adjust respective fiber lengths, may adjust optical path lengths of the reference beams 105-1, 105-2, and 105-3 according to respective regions measured with the measuring beams 106-1, 106-2, and 106-3, and are controlled by the personal computer 125 through a variable device driver 185 included in the driver section 181.

Next, optical paths of the measuring beams 106-1, 106-2, and 106-3 are described.

The measuring beams 106-1, 106-2, and 106-3 obtained by division by the optical couplers 131-1, 131-2, and 131-3 pass through the polarization controllers 153-4, are converted into parallel beams having a diameter of 1 mm by a lens 120-3 to be emitted, and enter the mirrors of the XY-scanner 119.

The lenses 120-1 and 120-3 are adjusted to align the center of each of the measuring beams 106-1, 106-2, and 106-3 with the center of rotation of the mirrors of the XY-scanner 119.

When the measuring beams 106-1, 106-2, and 106-3 enter the eye to be inspected 107, the measuring beams 106-1, 106-2, and 106-3 are reflected or scattered on the retina 127 to become the return beams 108-1, 108-2, and 108-3, pass through the optical couplers 131-1, 131-2, and 131-3, and are guided to the line camera 139.

Next, a structure of a measurement system of the OCT apparatus according to this embodiment is described.

Light intensities of combined beams 142-1, 142-2, and 142-3 are converted into voltages by the line camera 139 for each position (wavelength). To be specific, three interference fringes of spectral regions on wavelength axes, which correspond to the number of measuring beams 106-1, 106-2, and 106-3, are observed on the line camera 139.

The line camera 139 has 4,096 pixels. When 3,072 pixels of 4,096 pixels are used, the intensities of the scombined beams 142-1, 142-2, and 142-3 may be obtained for each wavelength (1,024 divisions).

Next, a method of acquiring tomographic images (OCT images) using the OCT apparatus is described with reference to FIGS. 8A to 8C.

In the OCT apparatus 100, the XY scanner 119 is controlled and the interference fringes are obtained by the line camera 139, to thereby simultaneously acquire three tomographic images of the retina 127. A method of acquiring the tomographic images (planes parallel to optical axis, namely, XZ-planes) of the retina 127 is described.

FIG. 8A illustrates a state in which the eye to be inspected 107 is observed by the OCT apparatus 100. As illustrated in FIG. 8A, when the measuring beams 106-1, 106-2, and 106-3 pass through the cornea 126 and enter the retina 127, the measuring beams 106-1, 106-2, and 106-3 are reflected or scattered in various positions to become the return beams 108-1, 108-2, and 108-3. Then, the return beams 108-1, 108-2, and 108-3 reach the line camera 139 with time delays in the respective positions.

The interference fringes which are information on the wavelength axis are converted into interference fringes on an optical frequency axis for the combined beams 142-1, 142-2, and 142-3 in view of the characteristics of the line camera 139 and the transmission type gratings 141. The interference fringes on the optical frequency axis, which are obtained by conversion, are subjected to inverse Fourier transformation to obtain information on a depth direction.

As illustrated in FIG. 8B illustrating only the measuring beam 106-2 for simplification, when an interference fringe is detected while the X-axis of the XY-scanner 119 is driven, the interference fringe is obtained for each position of the X-axis. In other words, the information on the depth direction may be obtained for each position of the X-axis.

As a result, a two-dimensional intensity distribution of the return beam 108-2 on the XZ-plane is obtained, which is the tomographic image.

As illustrated in FIG. 8C, when the XY-scanner 119 is controlled to raster-scan the retina 127 with the measuring beams 106-1, 106-2, and 106-3, the three tomographic images may be simultaneously obtained.

The case of scanning based on the assumption that the main scanning direction of the XY-scanner 119 is the Y-axis direction and the sub scanning direction thereof is the X-axis direction is described. As a result, the multiple YZ-plane tomographic images may be obtained.

The case of scanning without overlapping the measuring beams 106-1, 106-2, and 106-3 with one another is described. Overlap scanning may be performed for registration of the tomographic images.

The OCT image acquisition procedure is the same as in the first embodiment and thus the description thereof is omitted here. An adjusted optical path length of a corresponding reference beam is changed according to an interval between measuring beams on the fundus.

When the multiple measuring beams are used as described above, a large-area tomographic image may be acquired with ease by single scanning.

When optical path lengths of the multiple reference beams are separately controlled based on the interval between the measuring beams on the fundus, a large-area tomographic image may be acquired with ease by single scanning.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-056708 filed Mar. 12, 2010, which is hereby incorporated by reference herein in its entirety.

The invention claimed is:

1. An ophthalmologic imaging apparatus, comprising:
an irradiation unit configured to irradiate an eye to be inspected with a measuring beam;
a fixation lamp;
a lighting position changing unit configured to change a lighting position of the fixation lamp;
an optical path length difference changing unit configured to change an optical path length difference between the measuring beam and a reference beam corresponding to the measuring beam;
a control unit configured to control, when the lighting position of the fixation lamp is changed by the lighting position changing unit, the optical path length difference changing unit to change the optical path length difference with a changing amount corresponding to a changing amount of the lighting position of the fixation lamp; and
an acquisition unit configured to acquire a tomographic image of the eye to be inspected based on a beam obtained by combining the reference beam with a return beam from the eye to be inspected, which is irradiated with the measuring beam.

2. An ophthalmologic imaging apparatus according to claim 1, wherein the control unit controls, when the lighting position of the fixation lamp is changed, the optical path length difference changing unit to change the optical path length difference with a changing amount corresponding to both (a) the changing amount of the lighting position of the fixation lamp and (b) an eye axis length of the eye to be inspected.

3. An ophthalmologic imaging apparatus according to claim 1, further comprising a relative position changing unit configured to change, when the lighting position of the fixation lamp is changed, a relative position between the eye to be inspected and an optical system including an optical path of a measuring beam, by driving one of (a) an eye axis of the eye to be inspected and (b) the optical system with respect to the other of (a) and (b), with a changing amount corresponding to the changing amount of the lighting position of the fixation lamp.

4. An ophthalmologic imaging apparatus according to claim 1, wherein the acquisition unit is configured to acquire a tomographic image of the first observation region before the lighting position changing unit changes the lighting position of the fixation lamp, and is configured to acquire a tomographic image of the second observation region at the optical path length difference changed by the optical path length difference changing unit after the lighting position changing unit changes the lighting position of the fixation lamp in response to a change in the lighting position of the fixation lamp from a position corresponding to a first observation region of the eye to be inspected to a position corresponding to a second observation region of the eye to be inspected by the lighting position changing unit.

5. An ophthalmologic imaging method, comprising:
changing a lighting position of a fixation lamp;
changing an optical path length difference between the measuring beam and a reference beam corresponding to a measuring beam with a changing amount corresponding to a changing amount of the lighting position of the fixation lamp; and
acquiring a tomographic image of the eye to be inspected based on a beam obtained by combining the reference beam with a return beam from the eye to be inspected, which is irradiated with the measuring beam.

6. An ophthalmologic imaging apparatus, comprising:
an irradiation unit configured to irradiate an eye to be inspected with a measuring beam;
a relative position changing unit configured to change a relative position between the eye to be inspected and an optical system including an optical path of the irradiation unit, by driving one of (a) the eye to be inspected and (b) the optical system with respect to the other of (a) and (b);
an optical path length difference changing unit configured to change an optical path length difference between the measuring beam and a reference beam corresponding to the measuring beam, in accordance with a changing amount corresponding to a changing amount of the relative position changed by the relative position changing unit, when the relative position is changed; and
an acquisition unit configured to acquire a tomographic image of the eye to be inspected based on a beam obtained by combining the reference beam with a return beam from the eye to be inspected, which is irradiated with the measuring beams.

7. An ophthalmologic imaging apparatus according to claim 6, further comprising a lighting position changing unit configured to change a lighting position of a fixation lamp, and
wherein the relative position changing unit changes the relative position based on the lighting position of the fixation lamp changed by the lighting position changing unit.

8. An ophthalmologic imaging apparatus according to claim 6, wherein the optical path length difference changing unit changes the optical path length difference based on a characteristic of the eye to be inspected, when the relative position changing unit changes the relative position.

9. An ophthalmologic imaging apparatus, comprising:
an irradiation unit configured to irradiate an eye to be inspected with a measuring beam;
a relative position changing unit configured to change a relative position between an eye axis of the eye to be inspected and an optical axis of the irradiation unit;
an optical path length difference changing unit configured to change an optical path length difference between the measuring beam and a reference beam corresponding to the measuring beam;
a control unit configured to control the optical path length difference changing unit based on information representing a shape of the eye to be inspected when the relative position changing unit changes the relative position; and an acquisition unit configured to acquire a tomographic image of the eye to be inspected based on a beam obtained by combining the reference beam with a return beam from the eye to be inspected, which is irradiated with the measuring beams.

10. An ophthalmologic imaging method according to claim 5, wherein the optical path length difference changing unit changes the optical path length difference based on a characteristic of the eye to be inspected.

11. An ophthalmologic imaging method according to claim 5, further comprising a step of changing a relative position between an eye axis of the eye to be inspected and an optical axis of the measuring beam based on the changed lighting position of the fixation lamp.

12. An ophthalmologic imaging method according to claim 5, wherein, when the lighting position of the fixation lamp is changed from a position corresponding to a first observation region of the eye to be inspected to a position corresponding to a second observation region of the eye to be inspected, a tomographic image of the first observation region is acquired before the lighting position of the fixation lamp is changed, and a tomographic image of the second observation region at the changed optical path length difference is acquired after the lighting position of the fixation lamp is changed.

13. An ophthalmologic imaging method, comprising:
changing a relative position between an eye to be inspected and an optical system including an optical path of a measuring beam, by driving one of (a) the eye to be inspected and (b) the optical system with respect to the other of (a) and (b);
changing an optical path length difference between the measuring beam and a reference beam corresponding to the measuring beam, in accordance with a changing amount corresponding to a changing amount of the relative position; and
acquiring a tomographic image of the eye to be inspected based on a beam obtained by combining the reference beam with a return beam from the eye to be inspected, which is irradiated with the measuring beams.

14. An ophthalmologic imaging method according to claim 13, further comprising a step of changing a lighting position of a fixation lamp, and
wherein the relative position is changed based on the changed lighting position of the fixation lamp.

15. An ophthalmologic imaging method according to claim 13, wherein the optical path length difference is changed based on a characteristic of the eye to be inspected, when the relative position is changed.

16. An ophthalmologic imaging method, comprising:
changing a relative position between an eye axis of an eye to be inspected and an optical axis of an irradiation unit configured to irradiate the eye to be inspected with a measuring beam;
changing an optical path length difference between the measuring beam and a reference beam corresponding to the measuring beam;
controlling the optical path length difference based on an information representing a shape of the eye to be inspected when the relative position is changed; and
acquiring a tomographic image of the eye to be inspected based on a beam obtained by combining the reference beam with a return beam from the eye to be inspected, which is irradiated with the measuring beams.

17. A non-transitory tangible medium having recorded thereon a program for causing a computer to perform steps of the method according to claim 5.

18. A non-transitory tangible medium having recorded thereon a program for causing a computer to perform steps of the method according to claim 13.

19. A non-transitory tangible medium having recorded thereon a program for causing a computer to perform steps of the method according to claim 16.

20. An ophthalmologic imaging apparatus according to claim 1, further comprising
   a scanning unit configured to scan the measuring beam on a retina of the eye to be inspected with a cornea of the eye to be inspected as a pivot; and
   a display control unit configured to cause a display unit to display a tomographic image of the retina.

21. An ophthalmologic imaging apparatus according to claim 6, further comprising
   a scanning unit configured to scan the measuring beam on a retina of the eye to be inspected with a cornea of the eye to be inspected as a pivot; and
   a display control unit configured to cause a display unit to display a tomographic image of the retina.

22. An ophthalmologic imaging method according to claim 5, further comprising
   a step of scanning the measuring beam on a retina of the eye to be inspected with a cornea of the eye to be inspected as a pivot; and
   a step of causing a display unit to display a tomographic image of the retina.

23. An ophthalmologic imaging method according to claim 13, further comprising
   a step of scanning the measuring beam on a retina of the eye to be inspected with a cornea of the eye to be inspected as a pivot; and
   a step of causing a display unit to display a tomographic image of the retina.

* * * * *